(12) United States Patent
Schulman et al.

(10) Patent No.: US 7,967,869 B2
(45) Date of Patent: Jun. 28, 2011

(54) METHOD OF ATTACHING A STRAPLESS PROSTHETIC ARM

(75) Inventors: Joseph H. Schulman, Santa Clarita, CA (US); Charles L. Byers, Canyon Country, CA (US)

(73) Assignee: Alfred E. Mann Foundation For Scientific Research, Santa Clarita, CA (US)

( * ) Notice: Subject to any disclaimer, the term of this patent is extended or adjusted under 35 U.S.C. 154(b) by 1129 days.

(21) Appl. No.: 11/419,898

(22) Filed: May 23, 2006

(65) Prior Publication Data
US 2006/0293762 A1    Dec. 28, 2006

Related U.S. Application Data

(60) Provisional application No. 60/694,012, filed on Jun. 25, 2005.

(51) Int. Cl.
*A61F 2/66* (2006.01)
(52) U.S. Cl. .............................. 623/57; 623/33
(58) Field of Classification Search .......... 623/27–65
See application file for complete search history.

(56) References Cited

U.S. PATENT DOCUMENTS

| 5,425,763 | A | * | 6/1995 | Stemmann ................. 623/11.11 |
| 5,879,386 | A | | 3/1999 | Jore |
| 6,273,918 | B1 | | 8/2001 | Yuhasz et al. |
| 2003/0208269 | A1 | | 11/2003 | Eaton et al. |
| 2007/0162113 | A1 | * | 7/2007 | Sharkawy et al. ........... 623/2.38 |

FOREIGN PATENT DOCUMENTS

| DE | 43 28 779 A1 | 3/1994 |
| EP | 0 578 969 A2 | 1/1994 |
| WO | 2004 034934 A2 | 4/2004 |

* cited by examiner

*Primary Examiner* — Bruce E Snow
(74) *Attorney, Agent, or Firm* — Gary D. Schnittgrund

(57) ABSTRACT

Permanent magnets or electromagnets or a combination of such magnets are provided as a method to retain a prosthetic device on an extremity, such as an arm. The prosthesis utilizes the opposing forces, which are developed by virtue of like magnetic poles being in proximity to each other, to urge the prosthesis to remain attached to the extremity. The prosthesis is prevented from rotation by virtue of a centering force that is provided by an attachment magnet in the prosthesis being placed between two implanted magnets. A removable mounting ring is placed over the prosthesis straps to maintain them in proximity to the extremity.

2 Claims, 7 Drawing Sheets

METHOD OF ATTACHING A STRAPLESS PROSTHETIC ARM

CROSS REFERENCE TO RELATED APPLICATION

This application claims the benefit of U.S. Provisional Application Ser. No. 60-694,012, filed on Jun. 25, 2005.

FIELD OF THE INVENTION

The present invention relates to a method of attaching prosthetics, and, more specifically to an attachment method used in the donning/doffing and use of a socket on a residual limb. The present invention more particularly relates to an attachment method that utilizes magnets for mounting to the limb and that controls rotation of the mounted prosthesis.

BACKGROUND OF THE INVENTION

It has long been appreciated that differential air pressure or "suction" may be utilized to retain or "suspend" a prosthetic limb on an amputee's stump. Gravitational and other forces tend to cause separation between the prosthetic limb and the patient's residual extremity during use. This happens, for example, during the swing phase of gait, when a prosthetic leg is additionally subjected to centrifugal forces. Patients have worn a variety of belts, straps, cuffs and harnesses to retain prosthetic limbs against separation from the residual limb. Such devices are inconvenient and can cause chafing against the patient's body giving rise to sores and abrasions.

The manner in which an artificial limb is suspended or attached to the residual limb determines the amount of control an amputee has over the prosthesis. Suction suspension typically involves the utilization of a socket liner and a "hard" stump socket. The liner, which is usually fabricated from silicone, fits snugly over the residual limb and is enveloped by the socket. A negative pressure between the liner-sheathed stump and the interior of the socket holds the prosthesis on the limb. The suspension method is advantageous since it gives the amputee the ability to better control the prosthesis and provides for useful sensory or proprioceptive feedback. Suction suspension also makes the prosthesis feel lighter, compared to other forms of suspension.

A valve is employed to regulate the air pressure in the socket such that undesirable pressure differentials do not prevent or complicate the donning and doffing of the socket. The valve also maintains suction once the socket has been satisfactorily clad. During donning, the patient's liner-sheathed stump is inserted into the socket. At some stage or stages during the insertion the socket liner will form a roughly circumferential air-tight seal through contact with the hard socket. As the patient's stump is inserted further into the socket, air pressure increases under the stump. A valve permits air to escape from the socket until the pressure inside the socket equalizes with the ambient pressure and, hence, allows the stump to be fully inserted inside the socket. As a result, when the stump is completely inserted in the socket, the air pressure is equal inside and outside the socket. The valve is closed allowing no air to flow into the distal end of the stump socket. Any tendency to remove the stump from the socket creates a "suction" effect that acts to maintain the socket on the stump. In this manner, the prosthesis is held on the patient's stump. During doffing of the stump from the socket the valve is opened to equalize the ambient pressure and the pressure inside the socket, thus dissipating the "suction" effect and allowing removal of the stump.

Though the principle of employing "suction" for "suspending" an artificial limb is clear, there are practical problems. One of these is the difficulty in providing a reliable and permanently effective seal at the proximal open end of the socket, this issue is important in maintaining the reduced pressure inside the socket. In some instances it is doubtful whether the suspending suctional force can independently support the weight of the lower limb prosthesis. This is problematic from a safety stand-point, because if the suspension fails, and there is no redundant or back-up support mechanism, the artificial limb could detach from the patient's stump.

U.S. Pat. No. 5,376,131 to Lenze, et al. discloses a socket with an elastic diaphragm that engages a patient's stump, and attempts to provide an effective seal, but the local constriction due to such a tight fitting diaphragm can result in impairment of circulation in the amputee's residual limb. Suspension sleeves, which are substantially elongated bands fabricated from a resilient material and envelop part of the stump and part of the outer socket, have been used to provide complementary mechanical support and may additionally function as a sealing means. Since these sleeves constrictingly grip the residual limb over a wide region they can limit limb movement or be uncomfortable.

Another approach has led to design of a socket liner which is attachable at its distal end to a socket or artificial limb. In this manner, the liner is mechanically secured and can provide additional suspension, if needed, or can play the role of a backup suspension means. Typically, the socket liner is equipped with a detachable attachment component, at its distal end, which mates with a locking device and hence secures the residual limb to an artificial limb. The locking devices employ a spring-loaded clutch mechanism or a pin-lock mechanism to lock to the liner attachment component. This attachment component is either a barb-shaped structure or a frictionally-retained pin. These attachment components can lock in a number of positions which affects the overall length of the prosthesis. Though this may be advantageous, it can make it difficult for the patient to consistently achieve the same prosthetic configuration when the residual limb and the artificial limb are articulated. Further, in this mode of limb suspension, the locking means and the valve means are autonomous entities which are separately invasive and additive in weight on the distal end of the socket.

Another type of suspension device is a roll-on suction socket. The suction socket, which is typically fabricated from silicone, is a long tubular structure with one open end. The distal end of the suction socket is attachable to a prosthesis via an attachment component and a locking device employing the same principle and design described above. During donning, the suction socket is turned inside out and rolled on to the residual stump, being careful to avoid trapping air between the skin of the limb and the suction socket. Since the suction socket creates/destroys a partial vacuum at its distal end during rolling-on/rolling-off of the socket the function of a valve is intrinsically incorporated into the donning/doffing technique. Thus, the suction socket is a simple and effective device to suspend a prosthesis. But, this can be misleading because the suction socket may not be sealingly gripped by the hard socket, thereby converting the suction socket to a "traction" socket. Thus, the prosthesis is suspended onto the residual limb by a combination of the frictional adhesive traction of the suction socket and the locking retention due to the locking device. This skin traction causes an undesirable "tethering" effect by pulling on the skin, thereby creating multiple skin problems. The length of the tube can also interfere with the mobility of the residual limb, especially in the case of below-knee amputees.

Once a desired suspension device has been assimilated into the prosthesis, the prosthesis must be laterally aligned with respect to the residual limb. A typical conventional method for alignment of a prosthesis involves the use of a multi-axis slide mechanism which adjusts with two degrees of freedom. The alignment is reached by adjusting the relative horizontal positioning between two plates, one of which is attached to the distal end of the socket and the other to the top end of the artificial limb. Each plate has a centrally located slot and the slots are perpendicularly oriented to one another. Once the proper alignment has been ascertained a fastening means, such as a nut/bolt/washer combination couples the residual limb with the artificial limb. Such an alignment mechanism can be hazardous. During use of the prosthesis the interface between the socket and the artificial limb is subjected to stresses and moments that can result in relative motion between the alignment plates, thus misaligning the prosthesis. In extreme cases, the coupling plates may become unfastened, thereby, placing the patient at risk. The conventional alignment device adds excess weight to the prosthesis as well as adding to the cost, since it is a complicated device which is fabricated from titanium. Also, the size of the alignment device undesirably adds to the overall length of the prosthesis, which can be problematic when accommodating long stump lengths.

Despite the large number of suspension options available, none act to eliminate rotation between the hard socket and the suction liner. A design called a "quad socket" has been also used. The quad socket is shaped in a square manner and forcing the "cylindrical" limb into this square receptacle makes the prosthesis less apt to rotate on the limb. This is not comfortable for the limb. Therefore, there has been a trend toward more naturally-shaped sockets, making rotation control even more difficult.

There is a need for an improved attachment system for prosthetics. Also, there is a need for improving retention of the stump in the socket without sacrificing the patient's comfort and without compromising expense, weight, or simplicity of use. There also is a need for improving rotation control, which will improve the patient's overall comfort and agility.

SUMMARY OF THE INVENTION

The invention is a method of attaching a prosthesis comprising at least one attachment magnet creating a repulsive force with an implanted magnet that retains said prosthesis on an extremity. The attachment magnet is comprised of samarium cobalt or neodymium iron boron. The attachment magnet is attached to an attachment flap of said prosthesis. The attachment magnet is retained against the extremity with a mounting ring. The prosthesis is rotationally controlled on the extremity by magnetic repulsive forces between an implanted non-linear anti-rotation magnet and an anti-rotation flap magnet.

The novel features of the invention are set forth with particularity in the appended claims. The invention will be best understood from the following description when read in conjunction with the accompanying drawings.

DETAILED DESCRIPTION OF THE PREFERRED EMBODIMENT

Figure 1:
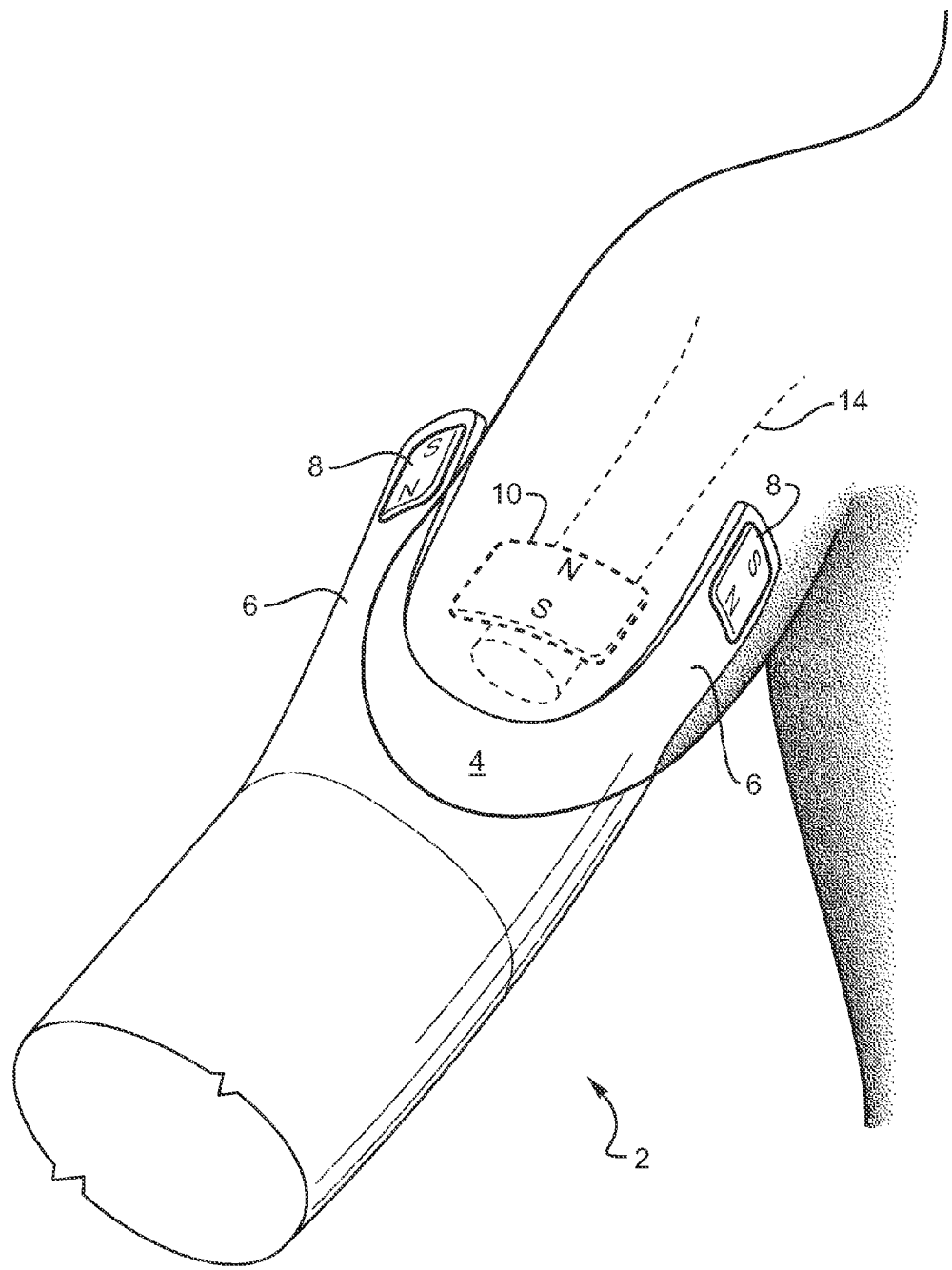
FIG. 1 illustrates a perspective view of an arm extremity and implanted magnet showing the prosthesis.

FIG. 1 provides a perspective view of a preferred embodiment of an arm extremity 4 with internal bone 14 and prosthesis 2. A magnet 10 is implanted in the extremity 4 to facilitate in retaining the prosthesis 2 on the extremity 4 by the magnetic repelling force generated by similar magnetic poles being placed facing each other of implanted magnet 10 and attachment magnets 8 that are securedly fastened in an attachment flap 6 of the prosthesis 2. In the illustration, the north poles of the implanted magnet 10 and of the attachment magnet 8 are repelling each other thereby urging the prosthesis 2 into retention on the extremity 4. Attachment flap 6 may be comprised of a rigid non-magnet rigid material such as a plastic or a flexible material such as a cloth.

The embodiment presented in FIG. 1 illustrates one implanted magnet 10, although it is preferable to have a plurality of implanted magnets 10 disposed at intervals around the extremity 4 to facilitate creation of an even mounting force on the top, bottom, and sides of the prosthesis 2 where it is in contact with the extremity 4. Similarly, two attachment flaps 6 and one attachment magnet 8 in each of the attachment flaps 6 is illustrated. It is preferable that the number of attachment flaps 6 be coordinated with the number and placement of implanted magnets 10 to assure that a constant and even mounting force is generated for retention of the prosthesis 2. While the attachment magnet 8 is presented as one magnet, it may in alternative embodiments be comprised of a plurality of magnets.

The illustrated implanted magnet 10 or the attachment magnet 8 may be permanent magnets, such as rare earth magnet, for example samarium cobalt (SmCo) or neodymium iron boron (NdFeB), they may be electromagnets, or they may be a combination of permanent or electromagnets to facilitate retention and mounting of the prosthesis 2. Samarium cobalt magnets are widely available and offer the advantages of being extremely strong, producible in a variety of simple or complex shapes and sizes, and being very resistant to corrosion. In addition, the magnets may be coated or plated with a protective biocompatible coating.

Neodymium iron boron generally exhibits poor corrosion resistance and is usually plated or coated, for example nickel plated, epoxy coated, or parylene coated. For implant applications, where biocompatibility is required, nickel is generally not an acceptable selection. Epoxy is not generally hermetic in the living tissue implant environment and is therefore not a preferred selection. Parylene is a known biocompatible coating material.

Other magnetic materials candidates include AlNiCo magnet alloy that is comprised of aluminum, nickel, cobalt, and iron. It has very good corrosion resistance. Ceramic magnet material (also known as ferrite or strontium ferrite) has a fair to good resistance to corrosion. Bonded or composite magnet materials may be made from Alnico, ceramic, NdFeB, or SmCo powders that are combined with a variety of plastic binders as a matrix. Lastly, flexible composite magnets are a mixture of ferrite or neodymium magnet powders and synthetic or natural rubber binders.

Figure 2:
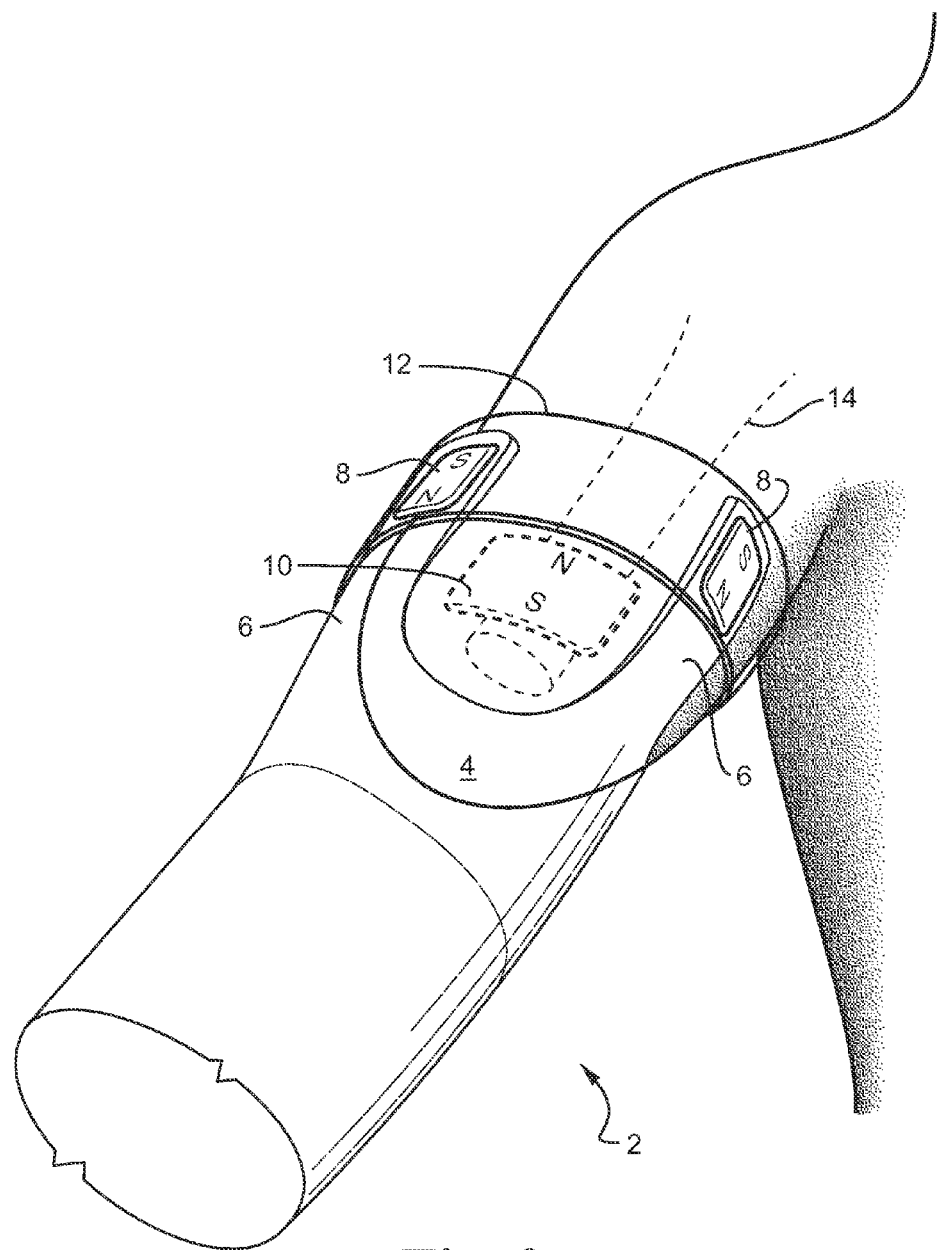
FIG. 2 illustrates a perspective view of an extremity and mounting ring.

An alternate embodiment is presented in FIG. 2 where the attachment flaps 6 are retained in the preferred position next to and in contact with the extremity 4 by mounting ring 12, which may be a contiguous band of material such as plastic or it may be a flexible strap design such as a strap. The mounting ring 12 is removable to facilitate placement of the prosthesis on extremity 4. The mounting ring 12 prevents the attachment flaps 6 from being repelled by implanted magnet 10 and by the repelling forces generated between the plurality of attachment magnets 8, which would move the flaps away from the extremity 4.

Figure 3:
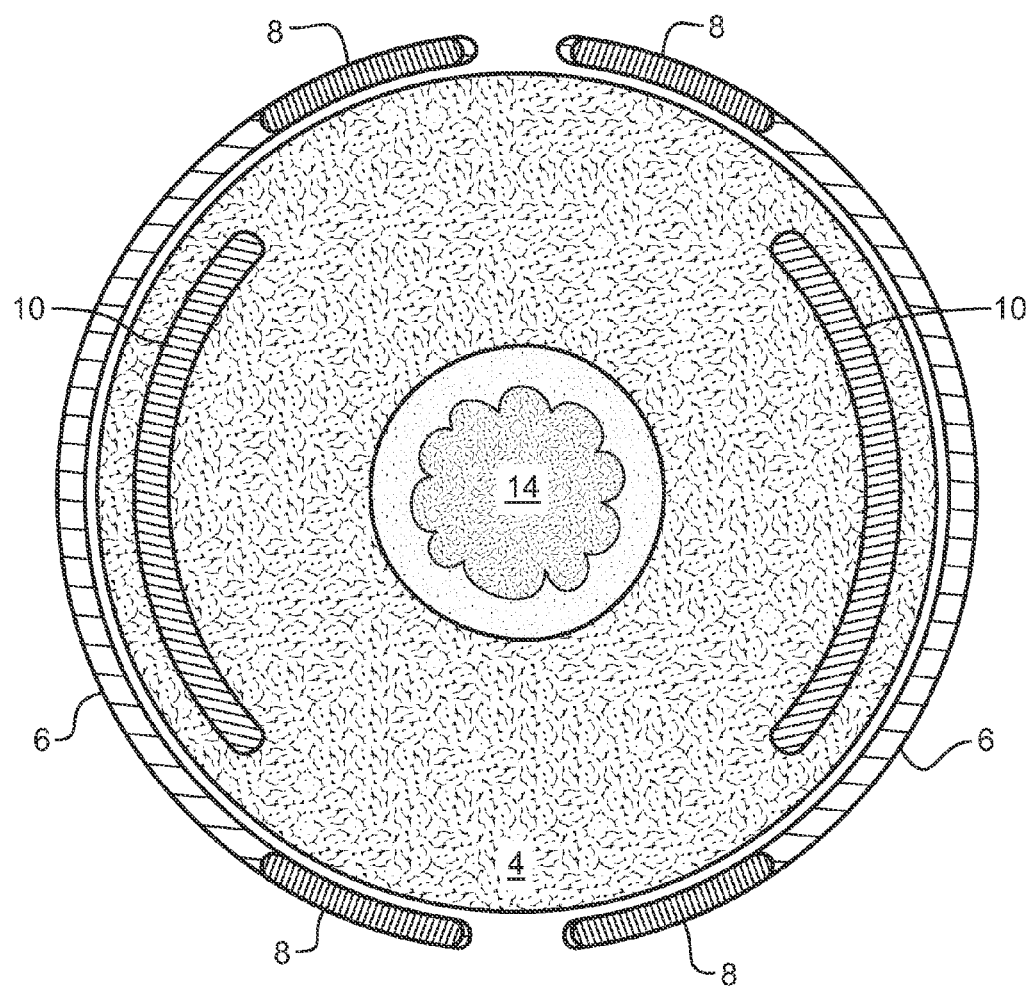
FIG. 3 illustrates a cross-sectional view of an extremity and attachment magnets.

The cross-section of extremity 4 and bone 14 (FIG. 3) illustrates one preferred positioning of the two attachment flaps 6 in hemispherical positions surrounding extremity 4. Two attachment magnets 8 are presented at opposing sides of the flaps 6 and are opposed by implanted magnet 10 thereby retaining the prosthesis 2 by magnetic repulsive forces.

Figure 4:
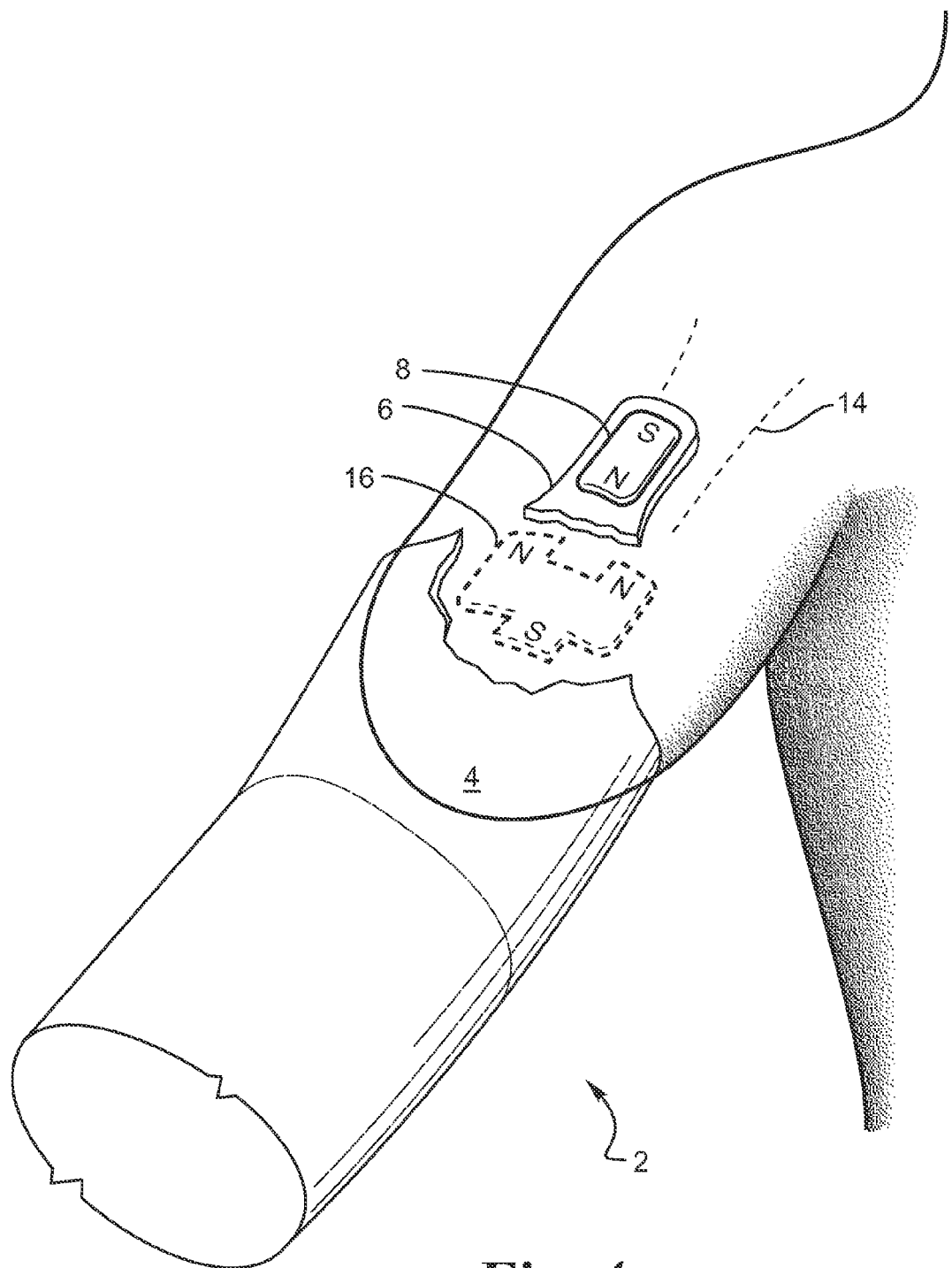
FIG. 4 presents an extremity and prosthesis with anti-rotation magnets.

In addition to retaining prosthesis 2 on extremity 4, the prosthesis is restrained to avoid rotation about extremity 4 when in the mounted position. Magnets are utilized to prevent rotation (FIG. 4) by virtue of non-linear anti-rotation magnet 16, which is implanted in extremity 4, where anti-rotation magnet 16 is shaped to present a biased repulsive force, as illustrated with the north magnet poles urging the like north magnetic pole of attachment magnet 8, that is securely mounted in attachment flap 6, to center itself between the north poles of anti-rotation magnet 16.

Figure 5:
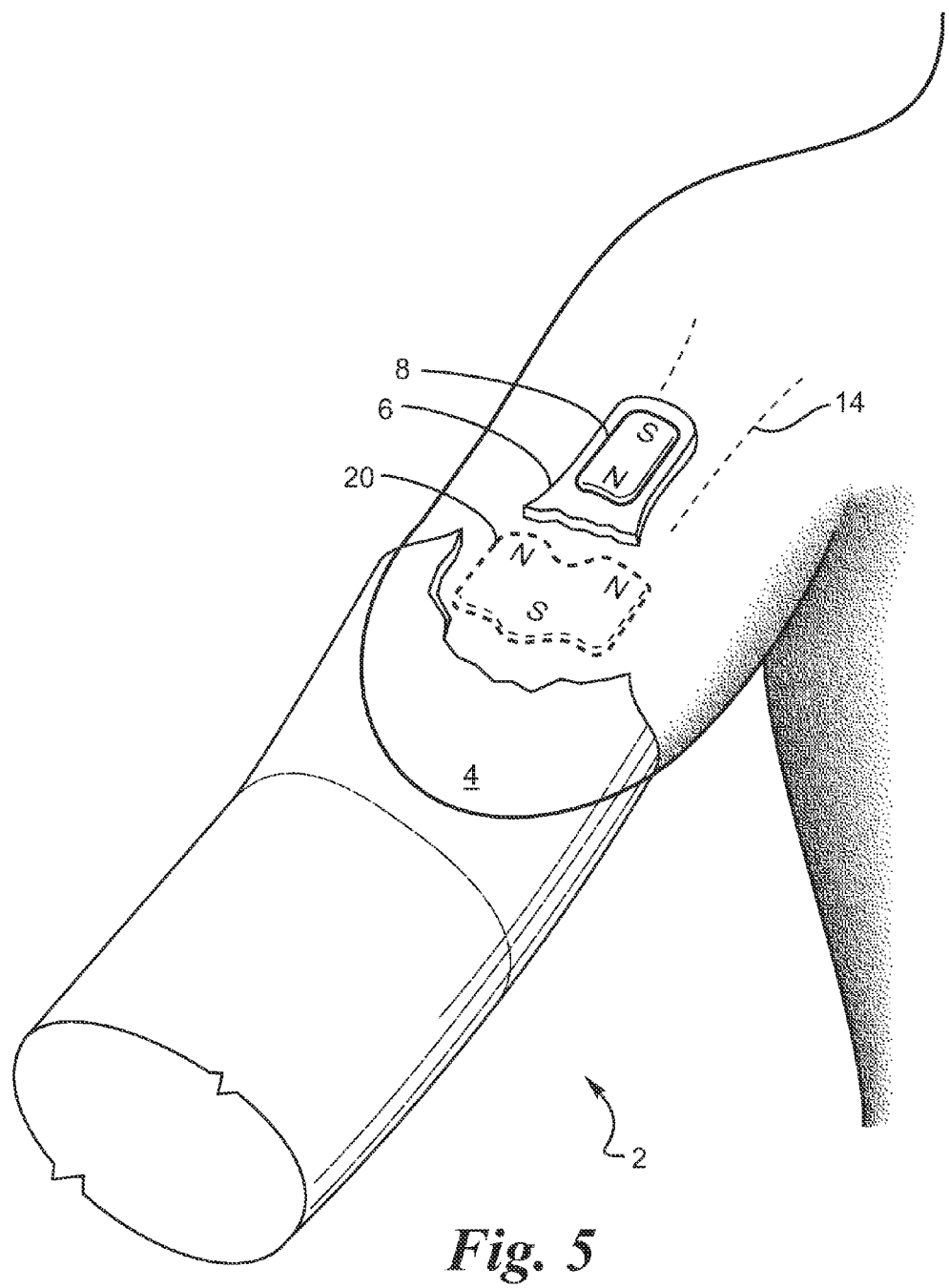
FIG. 5 presents an extremity and prosthesis with an alternative embodiment of anti-rotation magnets.

An alternate embodiment (FIG. 5) presents an implanted wavy anti-rotation magnet 20 where the anti-rotation mounting feature has been described, but the magnet centering force is provided by magnet 20 that presents raised north poles to center attachment magnet 8.

Figure 6:
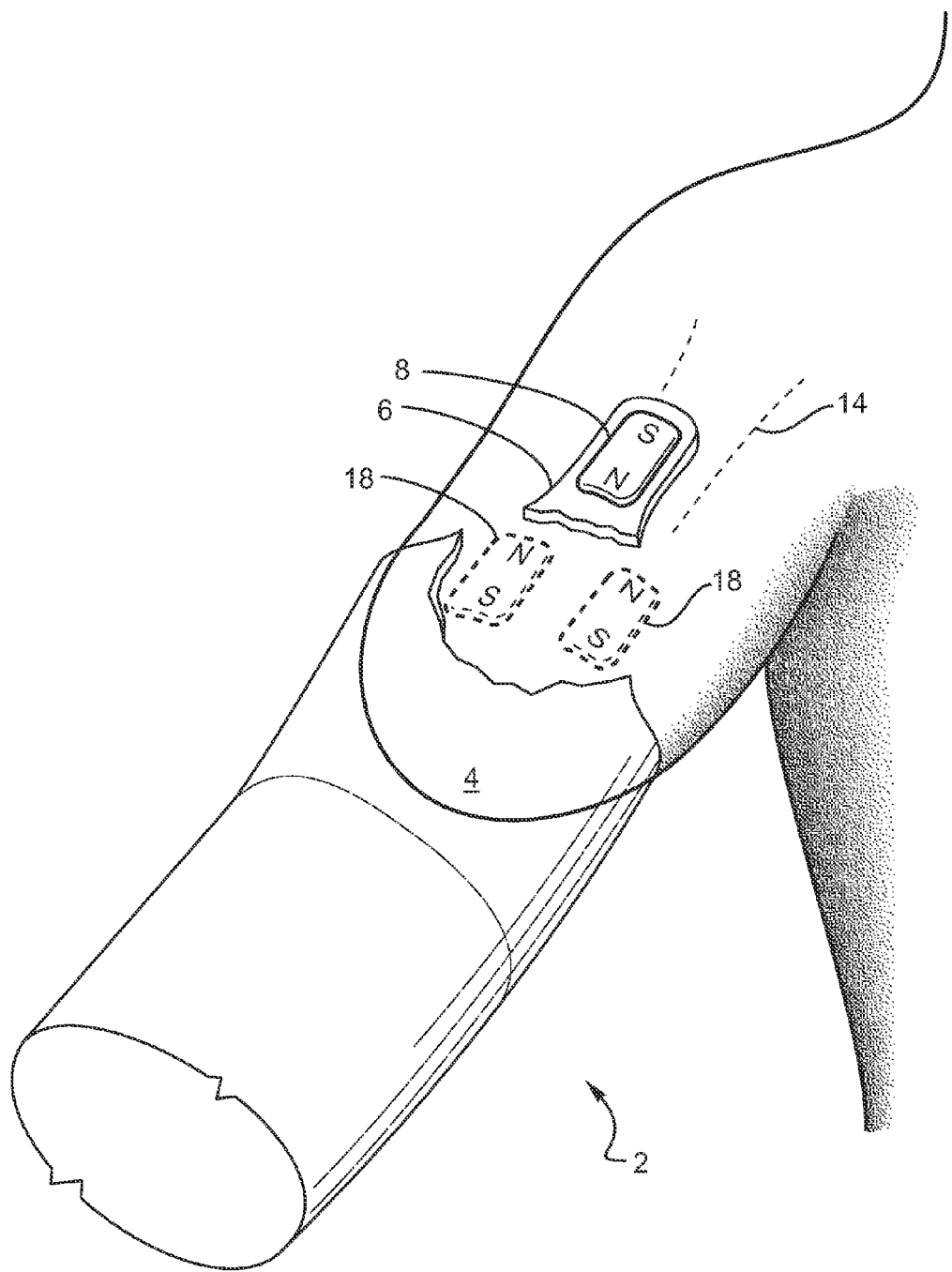
FIG. 6 presents an extremity and prosthesis with alternative implanted anti-rotation magnets.

A further alternate anti-rotation embodiment is presented (FIG. 6) where the centering magnetic force is provided by a plurality of implanted anti-rotation magnets 18 that operate as discussed previously. While two anti-rotation magnets 18 are illustrated, more than two magnets may be utilized to optimize the anti-rotation feature of the invention.

Figure 7:
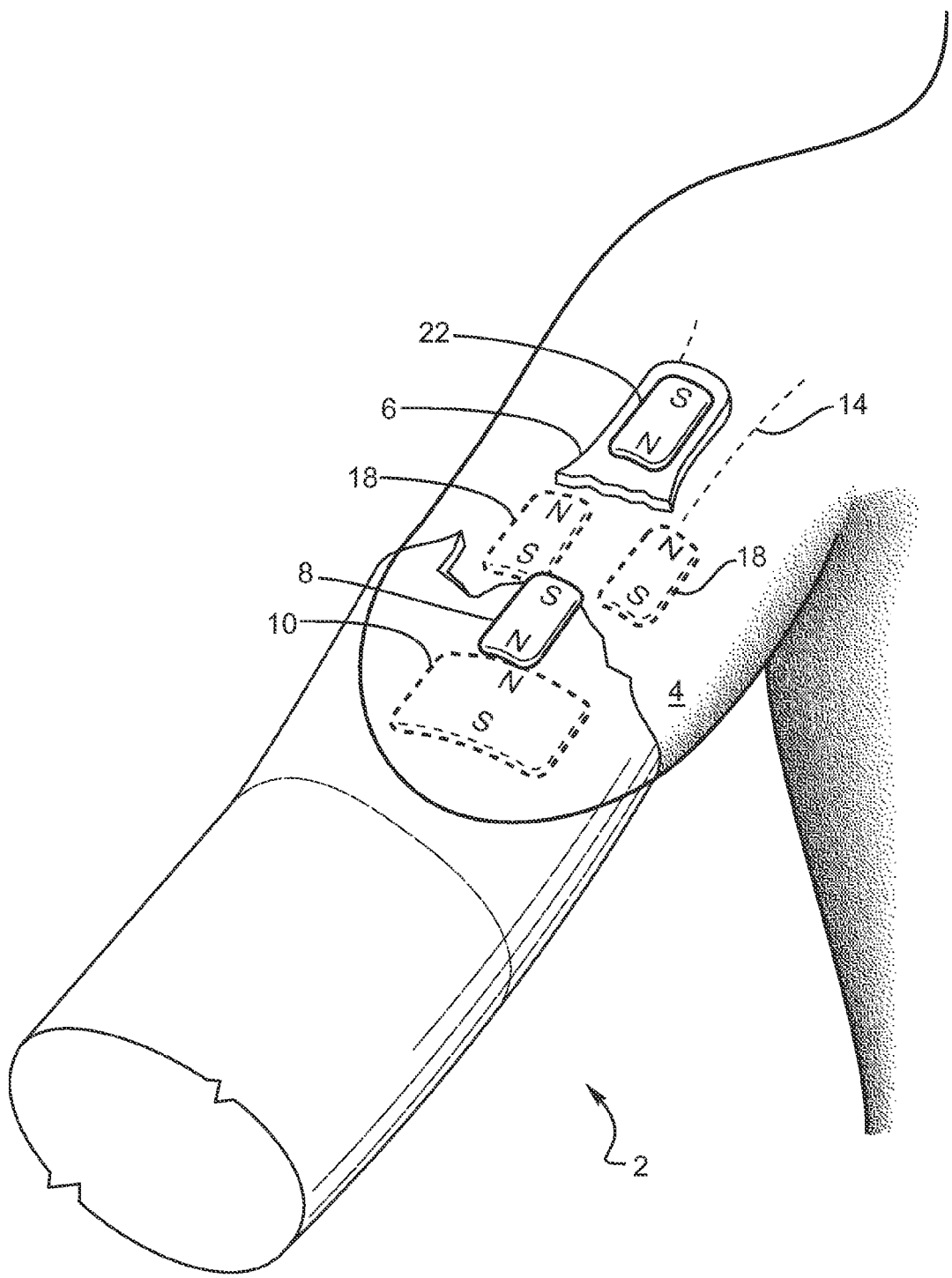
FIG. 7 presents a perspective view of an extremity and prosthesis with a combination of attachment magnets and anti-rotation magnets.

An integrated magnetic mounting retention and anti-rotation prosthesis 2 is illustrated (FIG. 7) wherein attachment flap 6 retains attachment magnet 8 which is repelled by the like-poled implanted magnet 10. The prosthesis 2 is prevented from rotation by the opposing magnetic forces provided by interaction between anti-rotation flap magnet 22 and the like-poled implanted anti-rotation magnets 18. In a preferred embodiment, at least two attachment flaps 6 provide balancing mounting and anti-rotation forces to retain prosthesis 2 on extremity 4.

Obviously, many modifications and variations of the present invention are possible in light of the above teachings. It is therefore to be understood that, within the scope of the appended claims, the invention may be practiced otherwise than as specifically described.

What is claimed is:

1. A method of retaining a prosthesis (2) having an attachment flap (6) comprising the steps of:
   selecting at least one implantable magnet (10) that is comprised of rare earth;
   selecting at least one attachment magnet (8) that is comprised of rare earth;
   implanting at least one of said implantable magnets (10);
   orienting at least one of said attachment magnets (8) on said attachment flap (6) of said prosthesis (2) to magnetically repel said at least one implantable magnet (10); and
   retaining said attachment flap (6) with a mounting ring (12) that removably wraps around the extremity.

2. The method of claim 1 further comprising the steps of:
   implanting an implantable anti-rotation magnet (18) comprising at least two anti-rotation magnet poles; and
   orienting an anti-rotation flap magnet (22) on said attachment flap (6) having a repelling magnetic force between said anti-rotation magnet poles of said implantable anti-rotation magnet (18).

* * * * *